(12) United States Patent
Kroll et al.

(10) Patent No.: US 7,171,268 B1
(45) Date of Patent: *Jan. 30, 2007

(54) IMPLANTABLE CARDIAC STIMULATION DEVICE PROVIDING ACCELERATED DEFIBRILLATION DELIVERY AND METHOD

(75) Inventors: Mark W. Kroll, Simi Valley, CA (US); James E. Brewer, Lino Lakes, MN (US)

(73) Assignee: Pacesetter, Inc., Sylmar, CA (US)

( * ) Notice: Subject to any disclaimer, the term of this patent is extended or adjusted under 35 U.S.C. 154(b) by 357 days.

This patent is subject to a terminal disclaimer.

(21) Appl. No.: 10/746,298

(22) Filed: Dec. 24, 2003

(51) Int. Cl.
*A61N 1/00* (2006.01)
(52) U.S. Cl. ......................................................... 607/5
(58) Field of Classification Search ................... 607/4, 607/5, 7, 9, 14
See application file for complete search history.

(56) References Cited

U.S. PATENT DOCUMENTS

| | | | |
|---|---|---|---|
| 5,292,348 A | 3/1994 | Saumarez et al. | 607/5 |
| 5,379,776 A | 1/1995 | Murphy et al. | 128/705 |
| 5,755,737 A | 5/1998 | Prieve et al. | 607/4 |
| 5,817,134 A | 10/1998 | Greenhut et al. | 607/14 |
| 5,843,133 A | 12/1998 | Routh et al. | 607/14 |
| 5,857,977 A | 1/1999 | Caswell et al. | 600/518 |
| 5,931,857 A | 8/1999 | Prieve et al. | 607/14 |
| 5,968,079 A | 10/1999 | Warman et al. | 607/5 |
| 6,128,528 A | 10/2000 | Ericksen et al. | 607/2 |
| 6,205,357 B1* | 3/2001 | Ideker et al. | 607/14 |
| 6,298,266 B1 | 10/2001 | Rubin et al. | 607/5 |
| 6,466,820 B1* | 10/2002 | Juran et al. | 607/9 |
| 6,671,548 B1 | 12/2003 | Mouchawar et al. | 607/14 |
| 2003/0120316 A1 | 6/2003 | Spinelli et al. | 607/14 |

FOREIGN PATENT DOCUMENTS

WO          WO 98/05254          2/1998

OTHER PUBLICATIONS

Kristina M. Ropella, et al., "The Coherence Spectrum—A Quantitative Discriminator of Fibrillatory and Nonfibrillatory Cardiac Rhythms", Circulation, 1989; vol. 80, No. 1:112-119.

* cited by examiner

*Primary Examiner*—George Manuel

(57) ABSTRACT

An implantable cardiac stimulation device provides accelerated delivery of defibrillation therapy to a patient's heart. The device includes a sensing circuit that provides right and left heart cardiac activity signals and a detector that detects an accelerated arrhythmia of the patient's heart and establishes a plurality of accelerated cardiac rate zones including a fibrillation rate zone and at least one intermediate rate zone. A classifier responsive to the right and left heart cardiac activity signals classifies an accelerated arrhythmia as one of fibrillation and tachycardia responsive to the detector detecting an accelerated arrhythmia having a cardiac rate within the at least one intermediate rate zones. A therapy circuit applies defibrillation to the heart responsive to the classifier classifying an accelerated arrhythmia as fibrillation and anti-tachycardia pacing to the heart responsive to the classifier classifying an accelerated arrhythmia as tachycardia.

20 Claims, 9 Drawing Sheets

IMPLANTABLE CARDIAC STIMULATION DEVICE PROVIDING ACCELERATED DEFIBRILLATION DELIVERY AND METHOD

CROSS-REFERENCE TO RELATED APPLICATIONS

This application is related to U.S. patent application Ser. No. 10/746,297, entitled "IMPLANTABLE CARDIAC STIMULATION DEVICE AND METHOD THAT DISCRIMINATES BETWEEN AND TREATS VENTRICULAR TACHYCARDIA AND VENTRICULAR FIBRILLATION"; and U.S. patent application Ser. No. 10/746,303, entitled "IMPLANTABLE CARDIAC STIMULATION DEVICE AND METHOD THAT DISCRIMINATES BETWEEN AND TREATS ATRIAL TACHYCARDIA AND ATRIAL FIBRILLATION," all applications filed Dec. 24, 2003.

FIELD OF THE INVENTION

The present invention generally relates to an implantable cardiac stimulation device and method that discriminates between and treats ventricular tachycardia and fibrillation. The present invention more particularly relates to such a device and method wherein such tachyarrhythmia discrimination is employed to enable accelerated delivery of defibrillation therapy.

BACKGROUND OF THE INVENTION

Implantable cardiac defibrillators (ICD's) are well known in the art. These devices, encapsulated in a conductive housing or enclosure, are generally implanted in a pectoral region of a patient and electrically connected to the heart with one or more electrode carrying leads. An arrhythmia detector detects accelerated arrhythmias, such as tachycardia or fibrillation. When such a tachyarrhythmia is detected, a pulse generator delivers electrical therapy to the patient's heart. A therapy for tachycardia may be anti-tachycardia pacing and a therapy for fibrillation may be a defibrillating shock. Such therapies are well known.

With ventricular tachycardia (VT) the ventricles of the heart beat abnormally fast. Though often unpleasant for the patient, a ventricular tachycardia is typically not immediately fatal. However, ventricular fibrillation (VF) is an immediately life threatening tachyarrhythmia, wherein the heart beats chaotically such that there is little or no net flow of blood from the heart to the brain and other organs.

With atrial tachycardia (AT), the atria of the heart beat rapidly at an abnormally high rate. This can cause the ventricular to in turn beat at a high rate. Cardiac output is downed. The patient may experience dizziness or feel fatigued. Although not immediately life threatening, it can also be unpleasant to a patient.

Atrial fibrillation is a common atrial tachyarrhythmia and can occur suddenly. It results in rapid and chaotic activity of the atrial of the heart. The chaotic atrial activity in turn causes the ventricular activity to become rapid and variable Although not life threatening, it is associated with strokes thought to be caused by blood clots forming in areas of stagnant blood flow as a result of prolonged atrial fibrillation. In addition to strokes, symptoms of atrial fibrillation may include fatigue, syncope, congestive heart failure, weakness and dizziness.

From the foregoing, it may be readily understood that it is most desirable to treat tachyarrhythmias as quickly as possible to return the heart to normal sinus rhythm (NSR). Tachycardia may be treated quite effectively with ATP while fibrillation generally requires a defibrillating shock. However, defibrillating shocks can cause discomfort and trauma to a patient while ATP is generally not perceptible. Hence, to achieve the most effective and the quickest return of tachyarrhythmias to NSR with the least amount of discomfort to the patient, it would be desirable to match the therapy to the tachyarrhythmia.

The need for therapy matching techniques becomes even more apparent in view of some recent research which has shown that the majority of very fast rhythms, normally treated as VF with a defibrillating shock, are actually monomorphic VT. These arrhythmias have traditionally been treated as a VF in ICDs because there was no reliable means of separating VFs, which require shocking, from VTs, which may be treated with ATP. Such research showed that approximately 50% of these high-rate tachyarrhythmias were, in fact, monomorphic tachycardias, and not VF.

Hence, there is a need in the art for an implantable cardiac stimulation device capable of distinguishing tachycardias from fibrillation and providing an appropriate therapy. There is also a need to accomplish the foregoing which assures that the patient is receiving the most appropriate therapy in the shortest possible time.

SUMMARY OF THE INVENTION

The invention provides an implantable cardiac stimulation device that treats accelerated arrhythmias of a patient's heart. The device comprises a sensing circuit that senses cardiac activity of a patient's right and left heart to provide first and second respective cardiac activity signals, a detector that detects an accelerated arrhythmia of the patient's heart, the detector establishing a plurality of accelerated cardiac rate zones including a fibrillation rate zone and at least one intermediate rate zone, a classifier responsive to the first and second cardiac activity signals that classifies an accelerated arrhythmia as one of fibrillation and tachycardia responsive to the detector detecting an accelerated arrhythmia having a cardiac rate within the at least one intermediate rate zone, and a therapy circuit that applies defibrillation to the heart responsive to the classifier classifying an accelerated arrhythmia as fibrillation and anti-tachycardia pacing to the heart responsive to the classifier classifying an accelerated arrhythmia as tachycardia. The intermediate rate zone is preferably a tachycardia rate zone.

The detector preferably detects accelerated ventricular arrhythmias. The sensing circuit senses cardiac activity of the right and left ventricles to provide the first and second cardiac signals, and the classifier includes a measuring circuit that measures relative correspondence between the first and second cardiac signals. The measuring circuit may be a coherer. The measuring circuit may alternatively be a correlator.

The invention further provides an implantable cardiac stimulation device for treating accelerated arrhythmias of a patient's heart. The device comprises sensing means for sensing cardiac activity of a patient's right and left heart to provide respective first and second cardiac signals, detecting means for detecting an accelerated arrhythmia of the patient's heart, the detecting means establishing a plurality of accelerated cardiac rate zones including a fibrillation rate zone and a tachycardia rate zone, classifying means for classifying an accelerated arrhythmia as one of fibrillation and tachycardia responsive to the detecting means detecting an accelerated arrhythmia having a cardiac rate within the tachycardia rate zones, and therapy means for applying defibrillation to the heart responsive to the classifying means classifying an accelerated arrhythmia as fibrillation and anti-tachycardia pacing to the heart responsive to the classifying means classifying an accelerated arrhythmia as tachycardia.

The invention further provides a method for use in an implantable cardiac stimulation device that treats accelerated arrhythmias of a patient's heart. The method comprises the steps of sensing cardiac activity of a patient's right and left heart to provide respective first and second cardiac signals, detecting an accelerated arrhythmia of the patient's heart, the detecting step including establishing a plurality of accelerated cardiac rate zones including a fibrillation rate zone and a tachycardia rate zone, classifying an accelerated arrhythmia as one of fibrillation and tachycardia responsive to detecting an accelerated arrhythmia having a cardiac rate within the tachycardia rate zones, and applying defibrillation to the heart responsive to classifying an accelerated arrhythmia as fibrillation and anti-tachycardia pacing to the heart responsive to classifying an accelerated arrhythmia as tachycardia.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
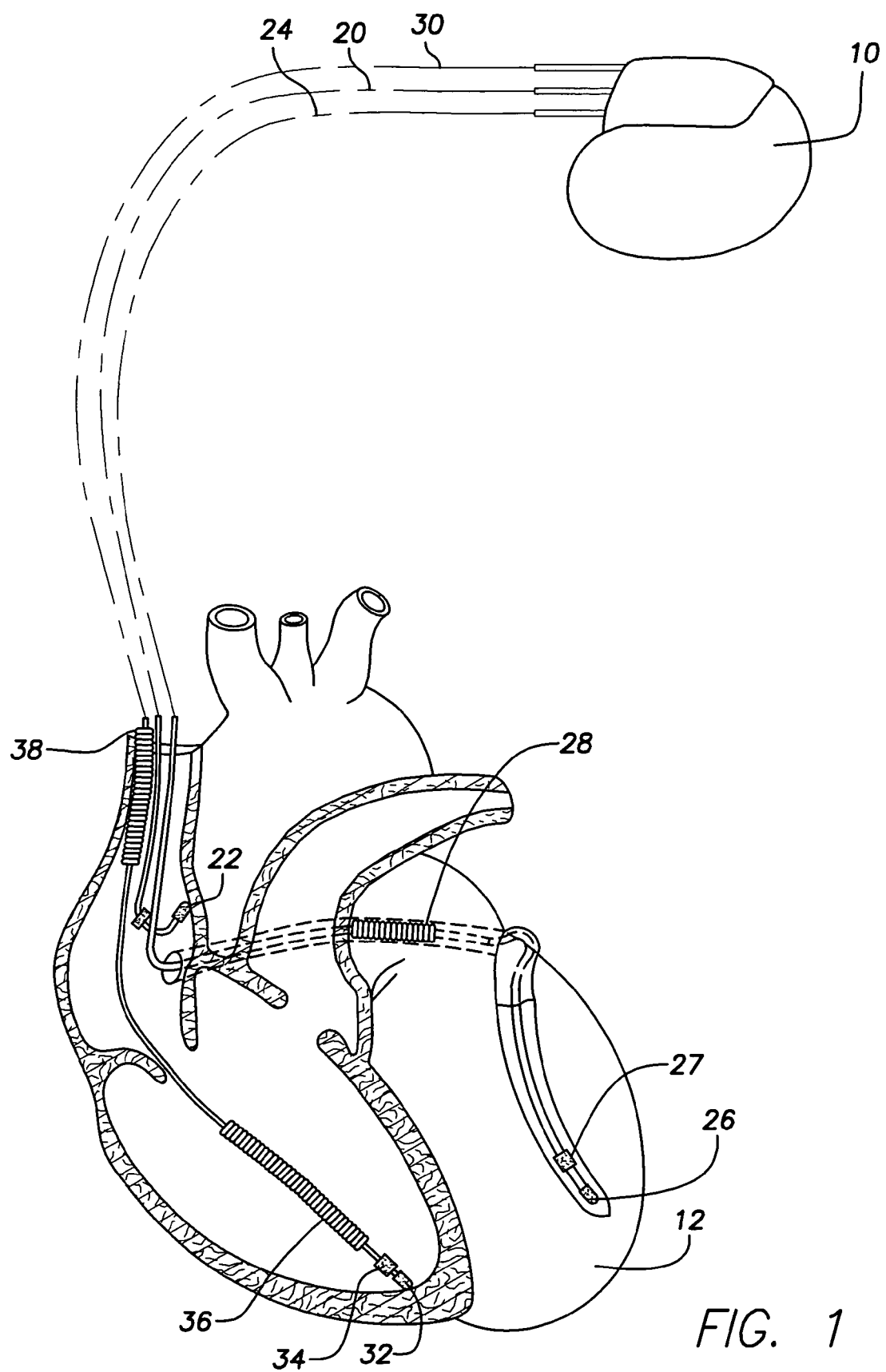
FIG. 1 is a simplified diagram illustrating an implantable stimulation device embodying the present invention in electrical communication with a patient's heart.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, a left ventricular ring electrode 27, and shocking therapy using at least a left atrial coil electrode 28. Electrodes 26 and 27 may be employed as a sensing electrode pair for sensing cardiac activity of the left ventricle in a bipolar mode. Alternatively, either electrode 26 or 27 may be used in a unipolar mode for sensing activity of the left ventricle.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Electrodes 32 and 34 may be employed for sensing cardiac activity of the right ventricle. Alternatively, either electrode 32 or 34 may be used in a unipolar mode for sensing activity of the right ventricle.

Figure 2:
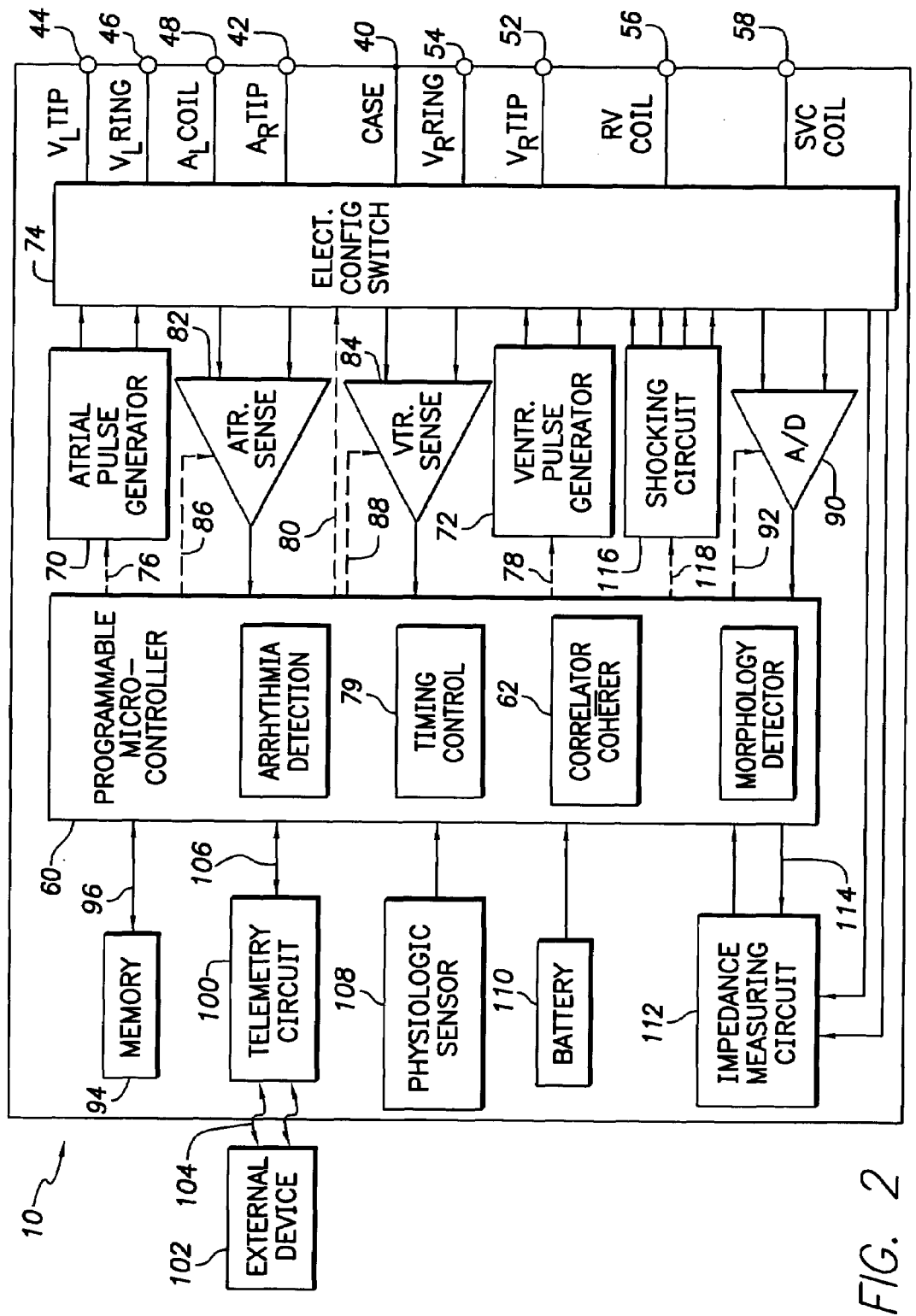
FIG. 2 is a functional block diagram of the implantable stimulation device of FIG. 1.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal (AR TIP) 42 adapted for connection to the atrial tip electrode 22.

To achieve left chamber sensing, pacing and shocking, the connector includes at least a left ventricular tip terminal ($V_L$ TIP) 44, a left ventricular ring terminal ($V_L$ RING) 46, and a left atrial shocking terminal ($A_L$ COIL) 48, which are adapted for connection to the left ventricular tip electrode 26, the left ventricular ring electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to predefined rate zones (i.e., bradycardia (BRADY), normal (NSR), low rate VT ($TACH_A$), high rate VT ($TACH_B$), extremely high rate VT (HYPER TACH) and fibrillation rate zones (FIB)) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries.

As further shown in FIG. 2, the device 10 is shown as having an impedance measuring circuit 112 which is enabled by the microcontroller 60 via a control signal 114. The impedance measuring circuit 112 is not critical to the present invention and is shown for only completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5–10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Now that the device 10 has been generally described, this description will now turn to those aspects of the device 10 that more particularly relate to the present invention. As previously mentioned, the device matches appropriate therapies with classified arrhythmias. While arrhythmia classification may be generally performed based upon rate alone, it has been found that high rate tachyarrhythmias, both ventricular and atrial, may be either a tachycardia or fibrillation. Hence, one important aspect of the present invention is the classification of tachycardias and fibrillation based upon characteristics other than rate. In accordance with the present invention, discrimination between high rate tachycardias and fibrillation is based upon the consideration that a tachycardia is a highly organized high rate rhythm while fibrillation is a highly chaotic high rate rhythm with virtually no organization. Hence, the relative correspondence between two cardiac signals may be measured. The measurement may then be used to classify a tachyarrhythmia as being either a tachycardia or fibrillation. For example, if the measure is above a predetermined standard, indicating relative organization, the arrhythmia is classified as a tachycardia and treated with an appropriate therapy, such as anti-tachycardia pacing (ATP), for example. However, if the measure is below the predetermined standard, indicating relative disorganization, the arrhythmia is classified as fibrillation and treated with an appropriate therapy, such as a defibrillating shock, for example.

To classify ventricular high rate tachyarrhythmias as either a high rate ventricular tachycardia or ventricular fibrillation, the cardiac signals from which relative correspondence is measured is preferably an electrogram of sensed right ventricular activity and an electrogram of sensed left ventricular activity. To classify atrial high rate tachyarrhythmia, as either a high rate atrial tachycardia or atrial fibrillation, the cardiac signals from which relative correspondence is measured is preferably an electrogram of a sensed P wave and an electrogram of an immediately succeeding P wave. The classification decision may be based upon a plurality of such measurements or a single measurement.

To determine relative correspondence, any measure of arrhythmia organization may be employed. In accordance with this embodiment, the measure of relative correspondence may be either a measured correlation or a measured coherence. To this end, the device further includes a correlator/coherer 62 to make the measurement. One particular coherence implementation is described hereinafter.

Figure 3:
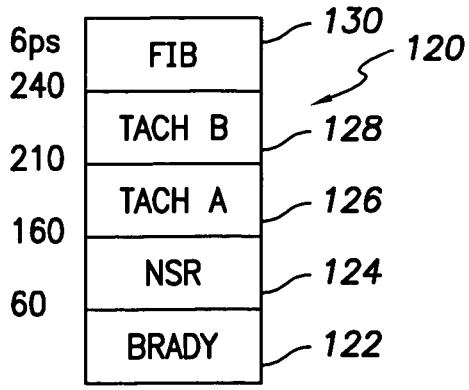
FIG. 3 is a simplified diagram of a conventional rate zone system.

In addition to classifying high rate arrhythmias as either tachycardia or fibrillation and providing a corresponding therapy, the present invention further contemplates the acceleration of defibrillation therapy. This is made possible because therapy selection is not based solely on cardiac rate. Reference to FIG. 3 shows a prior art or conventional rate zone system 120. The zone system 120 includes rate zones 122, 124, 126, 128, and 130. Rates below 60 beats per minute (bps) in zone 122 are considered bradycardia (BRADY) and treated with bradycardia pacing. Rates between 60 bps and 160 bps in zone 124 are considered normal sinus rhythm (NSR) and no therapy is delivered. Rates between 160 bps and 210 bps in zone 126 are considered to be a lower rate tachycardia (TACH A) and traditionally treated with anti-tachycardia pacing (ATP). Rates between 210 bps and 240 bps in zone 128 are considered to be a higher rate tachycardia (TACH B) and treated with more aggressive ATP. Finally, rates above 240 bps in zone 130 are considered fibrillation (FIB) and treated with a defibrillation shock. While the rate zones illustrated in FIG. 3 more particularly generally relate to ventricular arrhythmia classification, the foregoing also applies to atrial arrhythmias as well although the rate zone limits may be slightly different.

As will be noted in FIG. 3, an arrhythmia is not classified as fibrillation and treated with defibrillation therapy until the rate exceeds 240 bps. However, research has shown that a tachyarrhythmia have a rate less than about 240 bps, and for example, between 210 bps and 240 bps (zone 128 of FIG. 3) may be either tachycardia requiring ATP or fibrillation requiring defibrillation. Hence, a fibrillation having a rate between 210 bps and 240 bps (zone 128 in this example) would not be treated with defibrillation until sometime later after the rate has accelerated above 240 bps. However, by classifying the tachyarrhythmia as either tachycardia or fibrillation in a intermediate rate zone, such as zone 128, fibrillation therapy is accelerated and hence provided to the patient earlier then would be otherwise possible. This can be particularly important with ventricular fibrillation which is life threatening. Also, an early defibrillation attempt has the greatest chance of early defibrillation success. An early atrial defibrillation attempt is similarly rendered more likely successful and at lower defibrillation energies than might otherwise be required.

Figure 4:
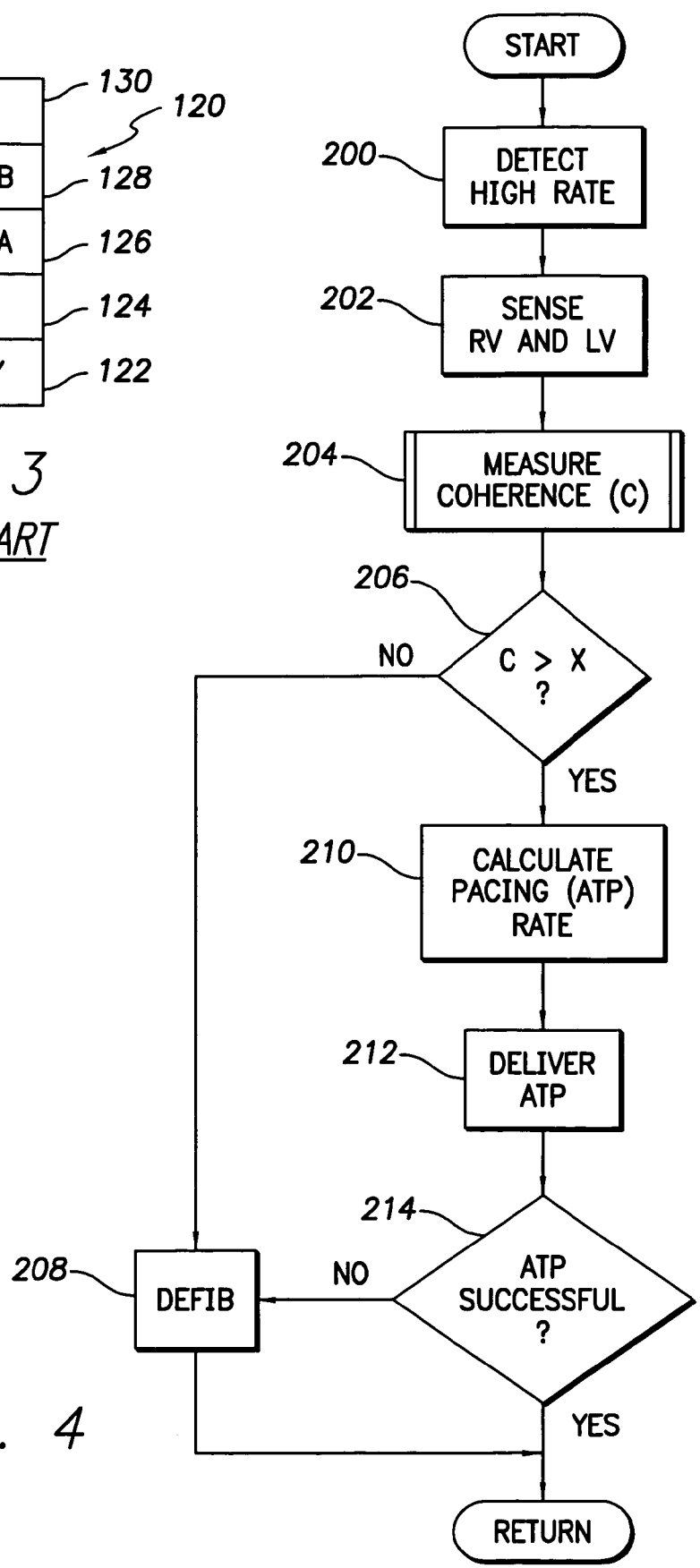
FIG. 4 is a flow chart describing an overview of the operation of one embodiment of the present invention.

In FIG. 4, a flow chart is shown describing an overview of the operation and novel features implemented in one embodiment of the device 10. In this flow chart, and the other flow charts described herein, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

The process of FIG. 4 initiates with the detection of a high cardiac rate falling in at least a tachycardia rate zone. The next activity block 202 is then implemented in a manner consistent with the methodology employed in implementing subroutine activity block 204. Activity block 204 calls for the measurement of the coherence between a right ventricular electrogram signal and a left ventricular electrogram signal. The coherence may be calculated using serial processing from stored signals or parallel processing using real time sensed signals. Hence, if serial processing is employed, the right and left electrogram signals may be stored in memory 94 by the data acquisition system 90 for later implementation of activity block 204. However, if parallel processing is employed, activity block 202 and activity block 204 may be implemented together. Such a coherence measurement process will be described subsequently.

After the coherence (C) is measured, the process proceeds to decision block 206 wherein the measured coherence (C) is compared to a predetermined standard (X). If the coherence is not greater than the predetermined standard, the tachyarrhythmia is classified as fibrillation and the process immediately advances to activity block 208 wherein defibrillation shock therapy is delivered to the heart. Following the defibrillation shock delivery of activity block 208, the process returns.

If the measured coherence is above the predetermined standard as determined in decision block 206, the tachyarrhythmia is classified a tachycardia and the process advances for delivery of ATP therapy. First, in activity block 210 the processor 60 calculates an appropriate pacing rate for ATP. This may be achieved using any one of many well known methods. The process then advances to activity block 212 for delivery of the anti-tachycardia pacing. After delivery of the ATP, the process advances to decision block 214 wherein it is determined if the ATP was successful in returning the heart to normal sinus rhythm (NSR). If the ATP was successful in returning the heart to NSR, the process returns. However, if the ATP was not successful in returning the heart to NSR, the process advances to activity block 208 for delivery of a defibrillation shock.

Figure 5:
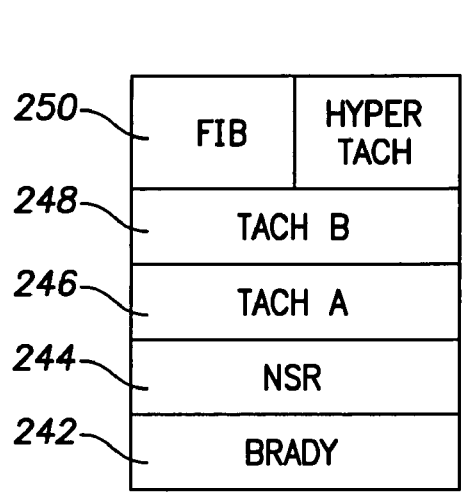
FIG. 5 is a simplified diagram of a rate zone system which may be employed to advantage in practicing the present invention.

Referring now to FIG. 5, it illustrates a cardiac rate zone system 240 embodying the present invention. The zone system 240 includes a bradycardia rate zone 242, a normal sinus rhythm rate zone 244, a low rate tachycardia rate zone 246, a high rate tachycardia rate zone 248, and a fibrillation/very high rate tachycardia rate zone 250. The zone rate system 240 illustrated in FIG. 5 provides for the discrimination and classification of tachyarrhythmias which would normally fall in a fibrillation rate zone. Hence, whenever a tachyarrhythmia is detected having a rate which falls within zone 250, the tachyarrhythmia is then classified, preferably using the relative correspondence between two electrogram signals, as either fibrillation or a very high rate tachycardia (HYPER TACH). If the tachyarrhythmia is classified a fibrillation, a defibrillation shock is delivered to the heart. If the tachyarrhythmia is classified as a very high rate tachycardia, the aggressive ATP is delivered to the heart.

Figure 6:
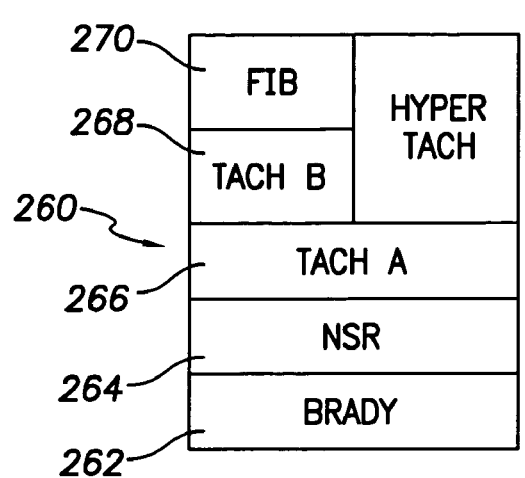
FIG. 6 is another rate zone system embodying the present invention.

FIG. 6 illustrates a further cardiac rate zone system 260 embodying the present invention. The zone rate system of FIG. 6 includes a bradycardia rate zone 262, a normal sinus rhythm rate zone 264, a low rate tachycardia rate zone 266, a high rate tachycardia rate zone 268, and a fibrillation rate zone 270. Here, if a tachyarrhythmia is detected having a rate falling within either the high rate tachycardia rate zone 268 or the fibrillation rate zone 270, the tachyarrhythmia is classified as either a tachycardia or a fibrillation. If, for example, the coherence is less than the predetermined standard, fibrillation therapy is provided to the heart in the form of a defibrillation shock. However, if the coherence is above the predetermined standard, aggressive ATP is applied to the heart for treating the classified tachycardia.

Figure 7:
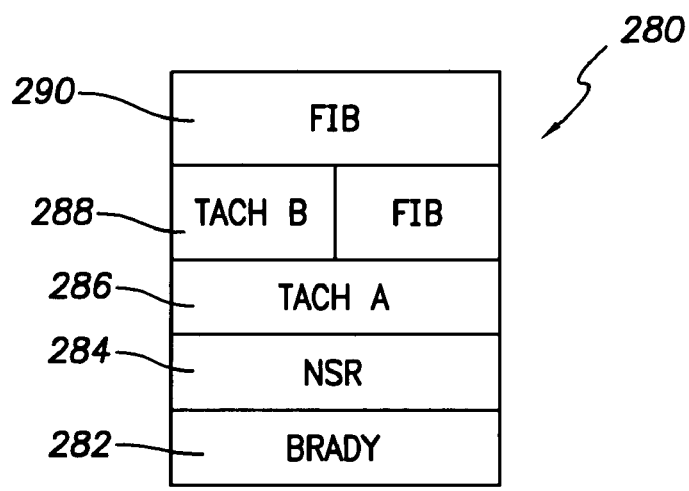
FIG. 7 is a still further rate zone system embodying the present invention.

FIG. 7 illustrates a still further cardiac rate zone system 280 embodying the present invention. It includes a bradycardia rate zone 282, a normal sinus rhythm rate zone 284, a low rate tachycardia rate zone 286, a high rate tachycardia rate zone 288, and a fibrillation rate zone 290. Here, if a tachyarrhythmia has a rate falling within the fibrillation rate zone 290, fibrillation therapy is applied to the heart. However, if a tachyarrhythmia is detected having a rate falling within the high rate tachycardia zone 288, the tachyarrhythmia is then classified. Hence, if the coherence is greater than the predetermined standard, ATP is applied to the heart. However, if the coherence is below the predetermined standard, fibrillation therapy is applied to the heart.

As will be noted in FIGS. 5, 6, and 7, the zone rate systems of FIGS. 6 and 7 provide accelerated defibrillation to the heart as compared to the zone rate system of FIG. 5. Hence, in accordance with the zone rate systems of FIG. 6 and FIG. 7, if a tachyarrhythmia is detected having a rate at least as fast as a high rate tachycardia, fibrillation therapy is an option should the tachyarrhythmia be classified as fibrillation. This is not possible with the zone rate system 240 of FIG. 5 wherein fibrillation therapy is not available to a tachyarrhythmia having a rate within the high rate tachycardia rate zone 248.

Figure 8:
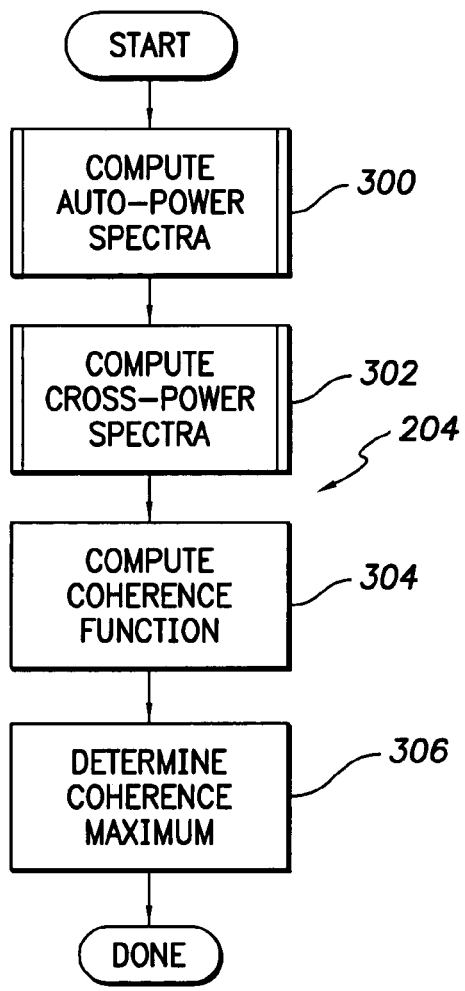
FIG. 8 is a flow chart describing the measure coherence sub-routine activity block of FIG. 4.
Figure 9:
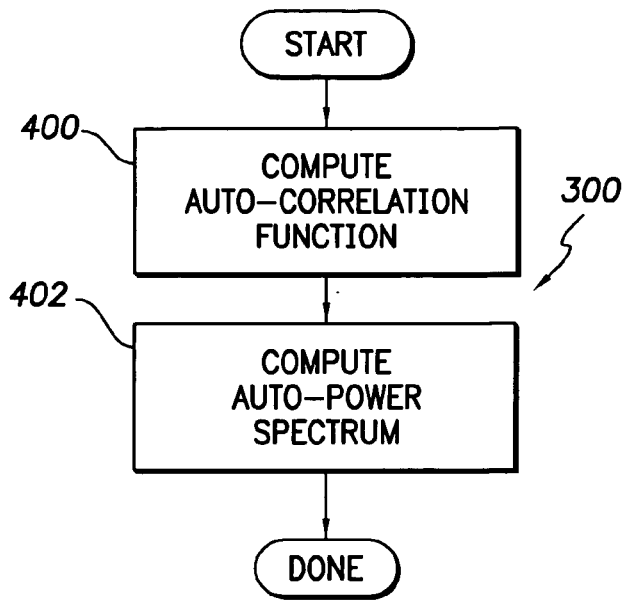
FIG. 9 is a flow chart describing the compute auto-power spectra sub-routine activity block of FIG. 8.
Figure 10:
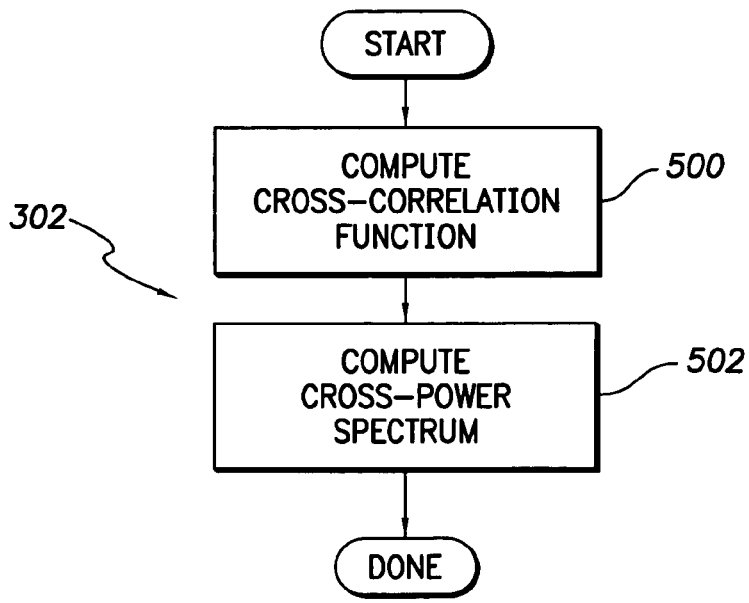
FIG. 10 is a flow chart describing the compute cross-power spectra subroutine activity block of FIG. 8.

Referring now to FIGS. 8, 9, and 10, these figures when taken together provide a flow chart describing a particular implementation of computer the coherence between two electrogram signals in practicing the present invention. FIG. 8 provides a flow diagram of the overall process of the subroutine activity block 204 of FIG. 4.

Activity blocks 300 and 302 of FIG. 8 may be implemented using serial processing or parallel processing. If serial processing is employed, the auto-power spectra of the right ventricular electrogram signal may first be computed followed by the computation of the auto-power spectra of the left ventricular electrogram signal. Next, the process then advances to activity block 302 wherein the cross-power spectra of the right ventricular electrogram signal and the left ventricular electrogram signal is computed.

If parallel processing is utilized, then auto-power spectra of the right ventricular electrogram signal and the auto-power spectra of the left ventricular electrogram signal may be computed together in parallel and parallel with the computation of a cross-power spectra of the right ventricular electrogram signal and left ventricular electrogram signal of activity block 302.

The process then advances to activity block 304 wherein the coherence function for two time series is computed. Following the computation of the coherence function in activity block 304, the process advances to activity block 306 wherein the coherence is measured from the coherence function. Preferably, the coherence used in making the subsequent comparison to the predetermined standard is the maximum value of the coherence function. The coherence measurement is completed with activity block 306 and the process completes.

FIG. 9 describes a manner in which the auto-power spectra of subroutine activity block 300 may be calculated. It begins at activity block 400 wherein the auto-correlation function of the right ventricular electrogram signal and the left ventricular electrogram signal is computed. This is followed by activity block 402 wherein the auto-power spectra is computed as a discrete-time cosine transform. The process then completes.

FIG. 10 describes a manner in which the cross-power spectra may be computed in accordance with the subroutine activity block 302 of FIG. 8. The process begins with activity block 500 wherein the cross-correlation function of the right ventricular electrogram signal and left ventricular electrogram signal is computed. This is followed by activity block 502 wherein the cross-power spectra as a discrete-time Fourier transform is computed. Once the processes of FIGS. 9 and 10 are completed, then the coherence function may be computed as represented by activity block 304 in FIG. 8.

By way of illustration only and not as a limitation, a more detailed treatment of FIGS. 8, 9, and 10 is provided below in the listing of MATLAB code for coherence function implementation and validation and which may be employed in practicing the present invention.

% construct magnitude squared coherence and coherence phase spectrum function [coherence, msq_coherence, coherence_phase_spec]=

. . .

coherence_detect_method (signal1, signal2, freq_scale)

Figure 11:
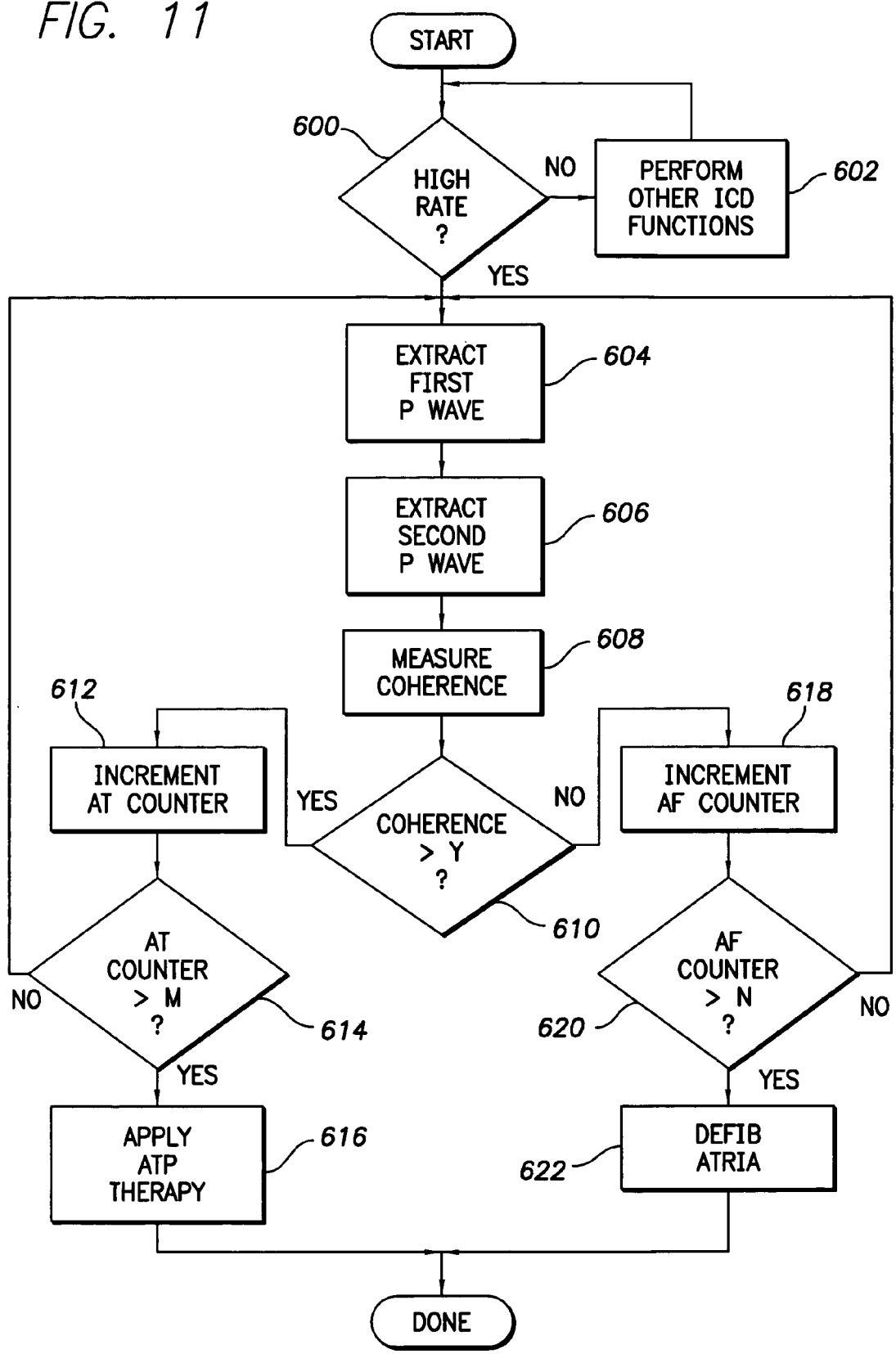
FIG. 11 is a flow chart describing an embodiment of the present invention wherein atrial tachyarrhythmias are classified.

% compute Fourier transform of each signal freq1=freq_scale.*fft(signal1);

freq2=freq_scale.*fft(signal2);

% compute complex modulus of product of 1ST frequency dom—signal with its conjugate freq_corr__11=abs(conj(freq1).*freq1);

% compute complex modulus of product of 2ND frequency dom—signal with its conjugate freq_corr__22=abs(conj(freq2).*freq2);

% compute complex modulus of product of conjugate of 1ST FD signal times 2ND FD signal cross_corr__12=(conj(freq1).*freq2);

% compute complex dimensionless coherence function (=nonnegative determinance)

coherence=cross_corr__12./(freq_corr__11.*freq_corr__22);

% compute magnitude squared coherence function (which must lie between 0 and 1)

msq_coherence=(abs(cross_corr__12).^2)./((freq_corr__11.^2).* ( freq_corr__22.^2));

% compute coherence phase spectrum (= phase lag of 2ND signal compared to 1ST signal)

coherence_phase_spec=atan(imag(coherence)./real (coherence));

Referring now to FIG. 11, it is a flow diagram illustrating a process embodying the present invention and by which atrial tachyarrhythmias may be classified as either an atrial tachycardia or atrial fibrillation in accordance with the present invention. Preferably, the device 10 continuously monitors atrial activity for detecting potential atrial tachyarrhythmias. To that end, atrial activity may be sensed in the right atrium with the lead 20. The atrial activity may be sensed with the data acquisition system 90 which continuously stores atrial activity in the memory 94. When an atrial tachyarrhythmia is detected in need of classification, the atrial activity stored in memory 94 may be utilized for use in determining relative correspondence between immediately successive P waves to support classification of the atrial tachyarrhythmia as either an atrial tachycardia or atrial fibrillation.

The process of FIG. 11 initiates with decision block 600 wherein it is determined if a high atrial rate has been detected. If a high atrial rate has not been detected, the process advances to activity block 602 for performing other ICD functions. However, if a high atrial rate has been detected requiring atrial tachyarrhythmia classification, the process advances to activity block 604 wherein a first P wave stored in memory 94 is extracted. In accordance with the immediately following activity block 606, a second P wave, immediately succeeding the first P wave, is also extracted. The first and second P waves are then, in accordance with activity block 608 provided to the correlator/coherer 62 for the measuring of coherence between the first signal representing the first P wave and the second signal representing the second P wave. The coherence between the P wave signals may be implemented in accordance with the coherence methodology previously described herein.

Once the coherence has been measured, the process advances to decision block 610 wherein it is determined if the coherence is greater than a predetermined standard. The outcome of this comparison may be utilized alone for classifying the atrial tachyarrhythmia. However, in accordance with further aspects of the present invention, a plurality of comparisons against a predetermined standard utilizing the measured coherence between successive P wave pairs are utilized. Hence, as may be noted in FIG. 11, if the coherence factor is greater than the predetermined standard as determined in decision block 610, an atrial tachycardia counter is incremented in activity block 612. After the atrial tachycardia counter has been incremented, the process advances to decision block 614 which determines if the count in the atrial tachycardia counter is greater than a first factor (M). If the count is not greater, the process returns for extracting another first and second P wave for coherence measurement. However, if the count in the atrial tachycardia counter is greater than the factor (M), the tachyarrhythmia is classified as an atrial tachycardia and the process advances to activity block 616 for the provision of anti-tachycardia pacing in the atria. After activity block 616, the process completes for detection of the next high rate.

If in decision block 610 it is determined that the coherence factor is not greater than the predetermined standard, the tachyarrhythmia is classifies as an atrial fibrillation and the process advances to activity block 618 wherein an atrial fibrillation counter is incremented. After the atrial fibrillation counter is incremented, the process advances to decision block 620 wherein it is determined if the AF counter is greater than a second factor (N). If the AF counter is not greater than the second factor, the process returns to activity block 604. However, if the atrial fibrillation counter count is greater than the second factor, the process then advances to activity block 622 for the delivery of a defibrillation shock to the atria. Once the atria are defibrillated, the process then completes.

Figure 12:
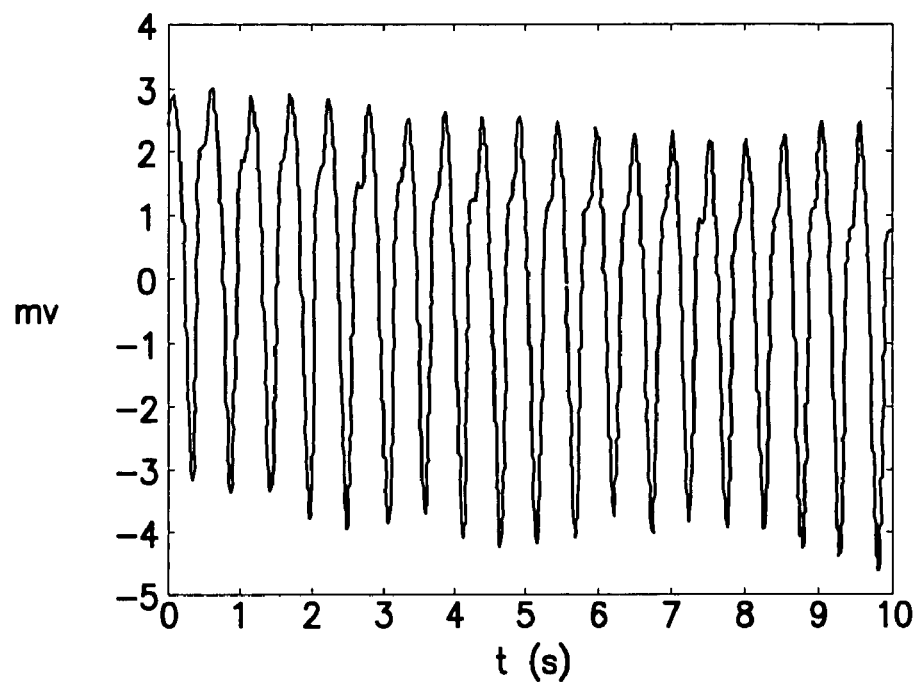
FIG. 12 is an electrogram signal of a ventricular tachycardia (VT) sensed from the right ventricle of a heart.
Figure 13:
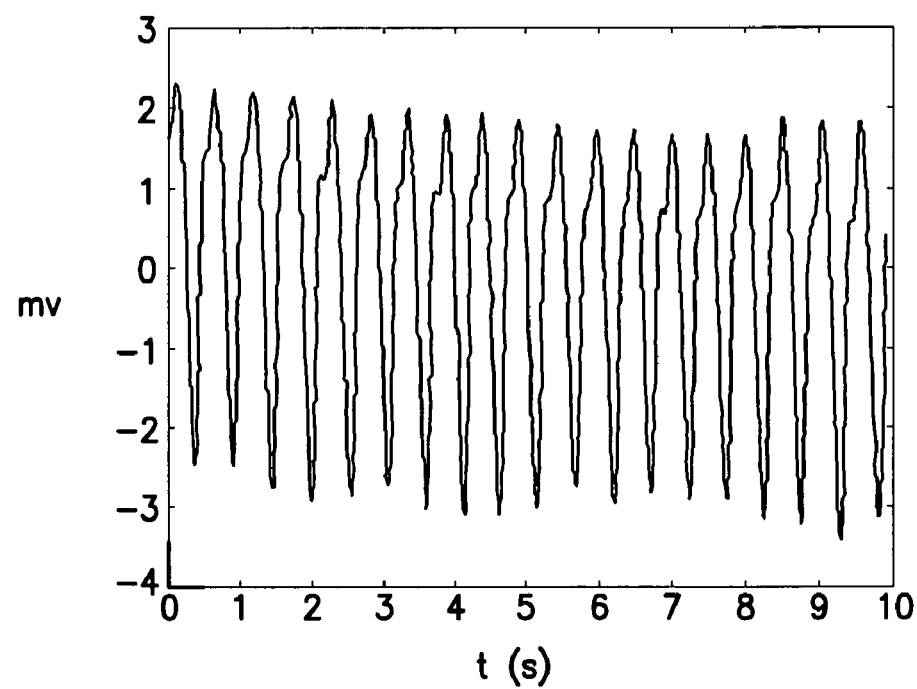
FIG. 13 is an electrogram signal of the VT sensed from the left ventricle.

FIG. 12 illustrates a right ventricular electrogram of a ventricular tachycardia. FIG. 13 represents the left ventricular electrogram of the same ventricular tachycardia. Both signals were sampled at 100 samples per second and low-pass filtered from 0.05 Hz to 50 Hz. Each electrogram illustrated is a 10 second strip recording.

Figure 14:
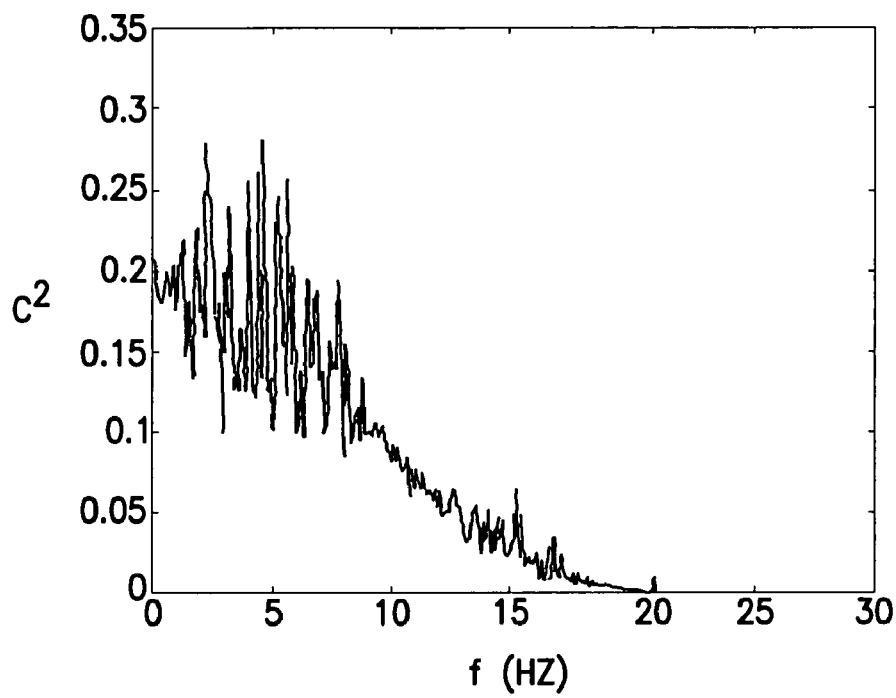
FIG. 14 is a plot of the magnitude squared coherence function of the signals of FIGS. 12 and 13.

FIG. 14 illustrates the magnitude squared coefficient function from DC to 25 Hz for the electrograms of FIG. 12 and FIG. 13. The signals have an approximate 50 millisecond shift in time between them representative of the propagating wave front. The maximum value for the coefficient function illustrated in FIG. 14 is 0.2808, indicating a significant frequency matching between the two electrograms.

Figure 15:
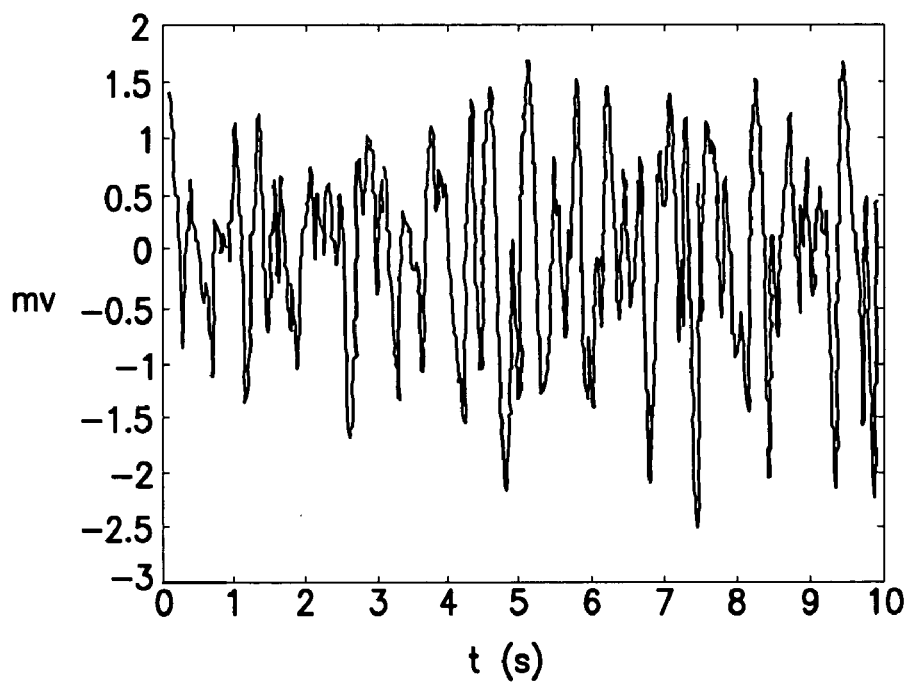
FIG. 15 is an electrogram signal of a ventricular fibrillation (VF) sensed from the right ventricle.
Figure 16:
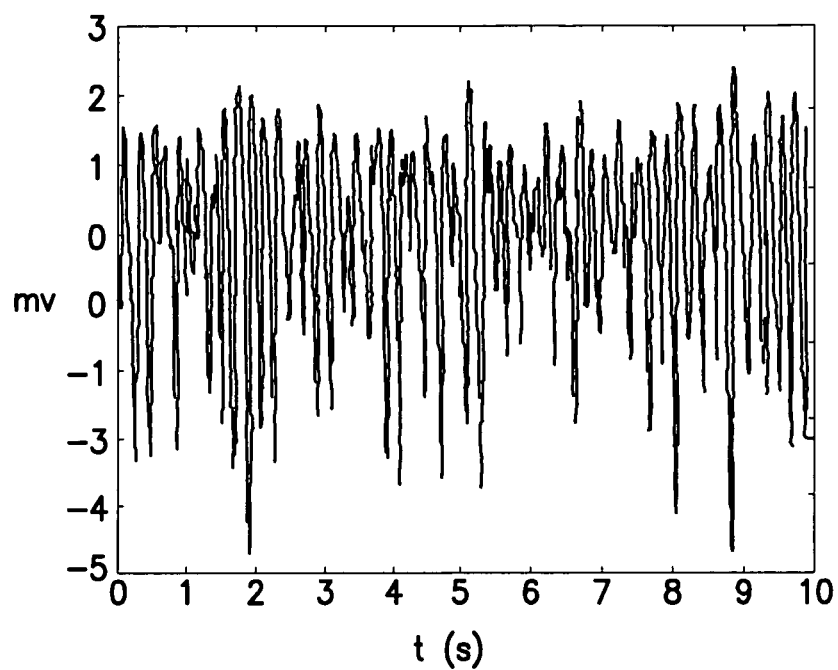
FIG. 16 is an electrogram signal of the VF sensed from the left ventricle.
Figure 17:
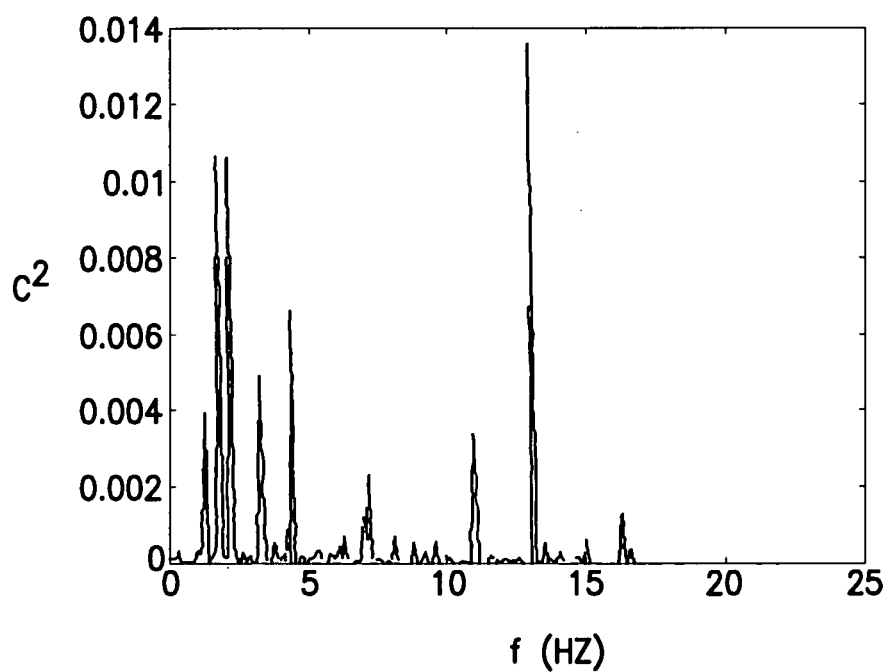
FIG. 17 is a plot of the magnitude squared coherence function of the signals of FIGS. 15 and 16.

FIG. 15 illustrates a right ventricular electrogram for a ventricular fibrillation. FIG. 16 represents a left ventricular electrogram for the same ventricular fibrillation. The electrograms were sampled at 100 samples per second and low-pass filtered from 0.05 Hz to 50 Hz. Each illustrated electrogram represents a 10 second recording strip. FIG. 17 illustrates the magnitude squared coefficient function from DC to 25 Hz for the ventricular fibrillation electrograms of FIGS. 15 and 16. The maximum value for the coefficient function is approximately 0.0013, indicating no significant frequency matching or relative correspondence between the two electrograms.

As will be noted between the coherence function of FIG. 14 for ventricular tachycardia and the coherence function of FIG. 17 for ventricular fibrillation that there is an extreme difference between the maximum coefficient measurements for the two tachyarrhythmias. This makes the relative correspondence between the electrogram signals, such as by measuring the coherence, a significant tool for classifying ventricular tachyarrhythmias as either a ventricular tachycardia or a ventricular fibrillation. Similar results are obtainable for atrial tachyarrhythmias.

While the invention has been described by means of specific embodiments and applications thereof, it is understood that numerous modifications and variations may be made thereto by those skilled in the art without departing from the spirit and scope of the invention. It is therefore to be understood that within the scope of the claims, the invention may be practiced otherwise than as specifically described herein.

What is claimed is:

1. An implantable cardiac stimulation device that treats accelerated arrhythmias of a patient's heart, the device comprising:
    a sensing circuit that senses cardiac activity of a patient's right and left heart to provide first and second respective cardiac activity signals;
    a detector that detects an accelerated arrhythmia of the patient's heart, the detector establishing a plurality of accelerated cardiac rate zones including a fibrillation rate zone and at least one intermediate rate zone;
    a classifier responsive to the first and second cardiac activity signals that classifies an accelerated arrhythmia as one of fibrillation and tachycardia responsive to the detector detecting an accelerated arrhythmia having a cardiac rate within the at least one intermediate rate zones; and
    a therapy circuit that applies defibrillation to the heart responsive to the classifier classifying an accelerated arrhythmia as fibrillation and anti-tachycardia pacing to the heart responsive to the classifier classifying an accelerated arrhythmia as tachycardia.

2. The device of claim 1 wherein the intermediate rate zone is a tachycardia rate zone.

3. The device of claim 1 wherein the detector detects accelerated ventricular arrhythmias.

4. The device of claim 3 wherein the sensing circuit senses cardiac activity of the right and left ventricles to provide the first and second cardiac signals, and wherein the classifier includes a measuring circuit that measures relative correspondence between the first and second cardiac signals.

5. The device of claim 4 wherein the measuring circuit is a coherer.

6. The device of claim 4 wherein the measuring circuit is a correlator.

7. An implantable cardiac stimulation device that treats accelerated arrhythmias of a patient's heart, the device comprising:
    a sensing circuit that senses right and left ventricular activity of a patient's heart to provide respective first and second ventricular activity signals;

a detector that detects an accelerated ventricular arrhythmia of the patient's heart, the detector establishing a plurality of accelerated cardiac rate zones including a ventricular fibrillation rate zone and at least one intermediate rate zone;

a classifier responsive to the first and second ventricular activity signals that classifies an accelerated ventricular arrhythmia as one of ventricular fibrillation and ventricular tachycardia responsive to the detector detecting an accelerated ventricular arrhythmia having a cardiac rate within the intermediate rate zone; and a therapy circuit that applies defibrillation to the ventricles of the heart responsive to the classifier classifying an accelerated ventricular arrhythmia as ventricular fibrillation and anti-tachycardia pacing to the ventricles of the heart responsive to the classifier classifying an accelerated ventricular arrhythmia as ventricular tachycardia.

8. An implantable cardiac stimulation device that treats accelerated ventricular arrhythmias of a patient's heart, the device comprising:

a sensing circuit that senses right and left ventricular activity of a patient's heart to provide respective first and second cardiac signals;

a detector that detects an accelerated ventricular arrhythmia of the patient's heart, the detector establishing a plurality of ventricular accelerated cardiac rate zones including a ventricular fibrillation rate zone and an intermediate rate zone;

a coherer that measures coherence between the first and second signals responsive to the detector detecting an accelerated ventricular arrhythmia having a cardiac rate within the intermediate rate zone;

a classifier responsive to the coherence measurement that classifies the detected ventricular accelerated arrhythmia as one of ventricular fibrillation and ventricular tachycardia;

a defibrillation circuit that applies ventricular defibrillation to the heart responsive to the classifier classifying an accelerated ventricular arrhythmia as ventricular fibrillation; and a pacing circuit that applies anti-tachycardia pacing to the heart responsive to the classifier classifying a ventricular accelerated arrhythmia as ventricular tachycardia.

9. An implantable cardiac stimulation device for treating accelerated arrhythmias of a patient's heart, the device comprising:

sensing means for sensing cardiac activity of a patient's right and left heart to provide respective first and second cardiac signals;

detecting means for detecting an accelerated arrhythmia of the patient's heart, the detecting means establishing a plurality of accelerated cardiac rate zones including a fibrillation rate zone and an intermediate rate zone;

classifying means for classifying an accelerated arrhythmia as one of fibrillation and tachycardia responsive to the detecting means detecting an accelerated arrhythmia having a cardiac rate within the intermediate rate zone; and therapy means for applying defibrillation to the heart responsive to the classifying means classifying an accelerated arrhythmia as fibrillation and anti-tachycardia pacing to the heart responsive to the classifying means classifying an accelerated arrhythmia as tachycardia.

10. The device of claim 9 wherein the classifying means classifies accelerated ventricular arrhythmias having rates also within the fibrillation rate zone.

11. The device of claim 9 wherein the detecting means detects accelerated ventricular arrhythmias.

12. The device of claim 11 wherein the sensing means senses cardiac activity of the right and left ventricles to provide the first and second cardiac signals, and wherein the classifying means includes measuring means for measuring relative correspondence between the first and second cardiac signals.

13. The device of claim 12 wherein the measuring means is a coherer.

14. The device of claim 12 wherein the measuring means is a correlator.

15. In an implantable cardiac stimulation device, a method of treating accelerated arrhythmias of a patient's heart, the method comprising:

sensing cardiac activity of a patient's right and left heart to provide respective first and second cardiac signals;

detecting an accelerated arrhythmia of the patient's heart, the detecting step including establishing a plurality of accelerated cardiac rate zones including a fibrillation rate zone and an intermediate rate zone;

classifying an accelerated arrhythmia as one of fibrillation and tachycardia responsive to detecting an accelerated arrhythmia having a cardiac rate within the intermediate rate zone; and applying defibrillation to the heart responsive to classifying an accelerated arrhythmia as fibrillation and anti-tachycardia pacing to the heart responsive to classifying an accelerated arrhythmia as tachycardia.

16. The method of claim 15 wherein the classifying step is also performed for accelerated arrhythmias having rates within the fibrillation rate zones.

17. The method of claim 15 wherein the detecting step includes detecting accelerated ventricular arrhythmias.

18. The method of claim 17 wherein the sensing step includes sensing cardiac activity of the right and left ventricles to provide the first and second cardiac signals, and wherein the classifying step includes measuring relative correspondence between the first and second cardiac signals.

19. The method of claim 18 wherein the measuring step includes measuring a coherence.

20. The method of claim 18 wherein the measuring step includes measuring a correlation.

* * * * *